(12) United States Patent
Connelly et al.

(10) Patent No.: US 7,794,660 B2
(45) Date of Patent: Sep. 14, 2010

(54) FLUID CONTENT MONITOR

(75) Inventors: Rowan Connelly, Fort Myers, FL (US); Joel Leal, Fort Myers, FL (US)

(73) Assignee: HF Scientific, Inc., Fort Myers, FL (US)

( * ) Notice: Subject to any disclaimer, the term of this patent is extended or adjusted under 35 U.S.C. 154(b) by 910 days.

(21) Appl. No.: 11/652,963

(22) Filed: Jan. 12, 2007

(65) Prior Publication Data

US 2007/0178010 A1    Aug. 2, 2007

Related U.S. Application Data

(60) Provisional application No. 60/758,799, filed on Jan. 13, 2006.

(51) Int. Cl.
*G01N 33/48* (2006.01)

(52) U.S. Cl. ............ 422/82.05; 422/68.1; 422/82.06; 422/82.07; 422/82.08; 422/82.09; 422/82.1; 422/82.11; 422/86; 422/119; 436/43; 436/47; 436/48; 436/49; 436/52; 436/164; 436/165; 436/171; 436/172; 436/805; 417/60; 417/204; 417/235; 417/254; 417/258

(58) Field of Classification Search ............ 422/68.1, 422/82.05–82.11, 86, 119; 423/462; 436/43, 436/47–49, 52–54, 101, 124, 125, 126, 164, 436/165, 171, 172, 805; 73/1.02, 1.03, 19.1; 417/60, 204, 235, 254, 258, 396–400
See application file for complete search history.

(56) References Cited

U.S. PATENT DOCUMENTS

| | | | |
|---|---|---|---|
| 3,953,136 A * | 4/1976 | Hach .......................... 356/410 |
| 4,288,308 A | 9/1981 | Hach |
| 4,553,532 A * | 11/1985 | Bohls .......................... 600/16 |
| 4,715,710 A | 12/1987 | Anderson |
| 4,865,992 A | 9/1989 | Hach et al. |
| 4,942,759 A | 7/1990 | Beers |
| 4,987,778 A | 1/1991 | Beers |
| 5,061,634 A | 10/1991 | Hickey et al. |
| 5,083,036 A | 1/1992 | Beers |
| 5,215,450 A * | 6/1993 | Tamari ....................... 417/474 |
| 5,259,537 A | 11/1993 | Beers et al. |
| 5,362,650 A | 11/1994 | Harp |

(Continued)

OTHER PUBLICATIONS

Hach Company, "CL17 Chlorine Analyzer Instrument Manual", Catalog No. 54400-18, Oct. 2001 3ed, 200,2001, pp. 1-71.

(Continued)

*Primary Examiner*—Jill Warden
*Assistant Examiner*—Shogo Sasaki
(74) *Attorney, Agent, or Firm*—Edwards Angell Palmer & Dodge LLP; George N. Chaclas

(57) ABSTRACT

A fluid content monitor including a cuvette, a calorimeter adapted to generate a signal indicative of contents of a fluid sample contained in the cuvette, a container for holding a reagent, and a pump assembly for delivering reagent from the container to the cuvette. The pump assembly includes a tube extending from the container to the cuvette, check valves preventing reverse flow in the tube, and a hammer driven by a solenoid for repetitively compressing the tube to pump reagent to the cuvette. The cuvette can be removed for cleaning and replacement.

13 Claims, 10 Drawing Sheets

U.S. PATENT DOCUMENTS

| | | |
|---|---|---|
| 5,446,544 A | 8/1995 | Beers |
| 5,738,500 A * | 4/1998 | Sundberg et al. ............ 417/204 |
| 6,180,412 B1 | 1/2001 | Kroll |
| 6,628,394 B2 * | 9/2003 | Huhta ........................ 356/402 |
| 6,749,091 B2 | 6/2004 | Connelly et al. |

OTHER PUBLICATIONS

Hach Company, "CL17 Chlorine Analyzer" fact sheet, 2001.
Hach Company, "Hach CL17 Chlorine Analyzer" specifications, brochure, 2005.
Hach Company, "CL17 Chlorine Analyzer" data sheet, 2005, pp. 1-4.

* cited by examiner

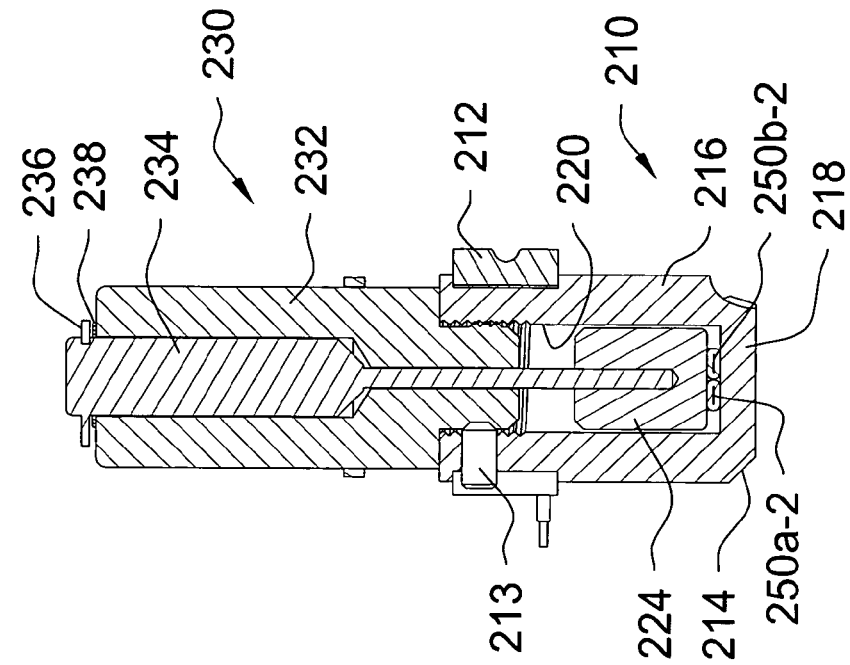
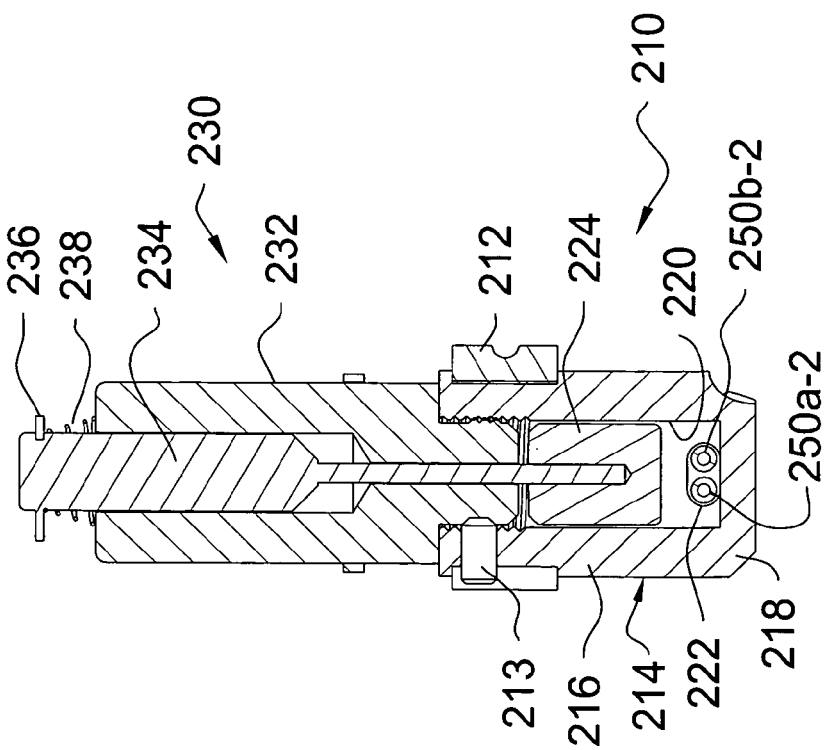
FIG. 8
FIG. 7

FLUID CONTENT MONITOR

CROSS-REFERENCE TO RELATED APPLICATION

This application claims priority to U.S. Provisional Patent Application No. 60/758,799, filed Jan. 13, 2006, which is incorporated herein by reference.

FIELD OF THE DISCLOSURE

The present disclosure relates to a fluid content monitor that can be used, for example, to monitor the residual chlorine level in drinking water, irrigation water, wastewater, and the like.

BACKGROUND OF THE RELATED ART

Various feed, dosing and metering pumps are known for delivering chemical additives to a supply of water or other liquid. Such pumps are particularly useful in fluid content monitors for adding reagents to test drinking, wastewater, and industrial water supplies for the presence of residual chlorine and other constituents. Conventionally, such monitoring has been performed using calorimetric reagent technology wherein a chemical reagent, such as DPD (N,N-diethyl-p-phenylenediamine), is dispensed into a test sample of water contained in a cuvette. The sample turns a certain hue, which depends upon the concentration of the chlorine in the water. This concentration is then photometrically determined by analyzing the hue with an appropriate electronic tester.

In order to obtain accurate test results, precisely measured amounts of reagent must be added to the test sample. Preferably, the reagents include an indicator chemical, such as DPD, and a buffer for adjusting the PH of the test sample. If the amounts of these reagents are not accurately controlled, erroneous measurements are likely to be taken. A dirty or damaged cuvette can also cause erroneous measurements.

What is still desired is a new and improved fluid content monitor that reliably and automatically delivers precisely measured doses of reagents to a water sample so that the sample may be accurately tested for the presence of selected constituent elements such as chlorine.

SUMMARY OF THE DISCLOSURE

Exemplary embodiments of the present disclosure provide a fluid content monitor including a chemical metering pump assembly that reliably and automatically delivers precisely measured doses of reagents to a water sample so that the sample may be accurately tested for the presence of selected constituent elements such as chlorine. The present disclosure also provides a fluid content monitor including a cuvette that can be easily removed without tools for cleaning or replacement.

In one embodiment, the fluid content monitor includes a cuvette, a calorimeter adapted to generate a signal indicative of contents of a fluid sample contained in the cuvette, a container for holding a reagent, and a pump assembly for delivering reagent from the container to the cuvette. The pump assembly includes a tube extending from the container to the cuvette, check valves preventing reverse flow in the tube, and a hammer driven by a solenoid for repetitively compressing the tube to pump reagent to the cuvette.

In another embodiment, the fluid content monitor includes a light transparent cuvette adapted to receive a fluid sample, a calorimeter adapted to direct light through the cuvette, receive the light passing through the cuvette, and generate a signal indicative of contents of the fluid sample based upon the received light, a container for holding a reagent and a pump assemble. Preferably, the pump assemble includes a body having a side wall extending from an end wall to define a chamber, and openings in the side wall adjacent the end wall, a hammer mounted within the chamber of the body for reciprocating linear movement between a retracted position moved away from the end wall and an extended position moved against the end wall, an actuator operatively connected to the hammer, a reagent tube extends from the container for delivering reagent to the cuvette, wherein a resiliently flexible section of the tube passes through the openings in the side wall of the pump body and extends through the chamber between the hammer and the end wall such that the resiliently flexible section is open when the hammer is in the retracted position and substantially closed when the hammer is in the extended position. In a further aspect, an inlet check valve is carried by the reagent tube between the reagent container and the pump to prevent reverse flow to the reagent container, and an outlet check valve is carried by the reagent tube between the pump and the cuvette to prevent reverse flow to the pump.

In another embodiment, the fluid content monitor includes a light transparent cuvette adapted to receive a fluid sample, a container for holding a reagent, a pump adapted to pump reagent from the reagent container to the cuvette and a colorimeter adapted to direct light through the cuvette, receive the light passing through the cuvette, and generate a signal indicative of contents of the fluid sample based upon the received light. The colorimeter preferably includes a body defining a cuvette portal for removably receiving the cuvette, and a passageway extending through the cuvette portal, and a nozzle removably secured in the passageway, wherein the nozzle is adapted to lock the cuvette in the passageway.

In still another embodiment, the fluid content monitor includes a light transparent cuvette adapted to receive a fluid sample, a nozzle connected to the cuvette for introducing reagent into the cuvette, a colorimeter adapted to direct light through the cuvette, receive the light passing through the cuvette, and generate a signal indicative of contents of the fluid sample based upon the received light, a first container for holding a first reagent, a second container for holding a second reagent and a pump assembly. The pump assembly includes a body having a side wall extending from an end wall to define a chamber, and openings in the side wall adjacent the end wall, a hammer mounted within the chamber of the body for reciprocating linear movement between a retracted position moved away from the end wall and an extended position moved against the end wall, an actuator operatively connected to the hammer, a first reagent tube is in fluid communication with the first container for delivering reagent to the cuvette, wherein a resiliently flexible section of the first reagent tube passes through the openings in the side wall of the pump body such that the respective resiliently flexible section is open when the hammer is in the retracted position and substantially closed when the hammer is in the extended position, a second reagent tube is in fluid communication with the second container for delivering reagent to the cuvette, wherein a resiliently flexible section of the second reagent tube passes through the openings in the side wall of the pump body such that the respective resiliently flexible section is open when the hammer is in the retracted position and substantially closed when the hammer is in the extended position, and an inlet check valve carried by the each reagent tube between the respective reagent container and the pump to prevent reverse flow to the reagent containers.

Additional aspects and advantages of the present disclosure will become readily apparent to those skilled in this art from the following detailed description, wherein only an exemplary embodiment of the present disclosure is shown and described, simply by way of illustration of the best mode contemplated for carrying out the present disclosure. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

Reference is made to the attached drawings, wherein elements having the same reference character designations represent like elements throughout, and wherein:

FIG. 7 is an enlarged cross-sectional view of the pump, the pump actuator, and the tubing, wherein a hammer of the pump is shown in a retracted position;

FIG. 8 is an enlarged cross-sectional view of the pump, the pump actuator, and the tubing, wherein the hammer is shown in an extended position compressing the tubing;

DETAILED DESCRIPTION OF EXEMPLARY EMBODIMENTS

Figure 1:
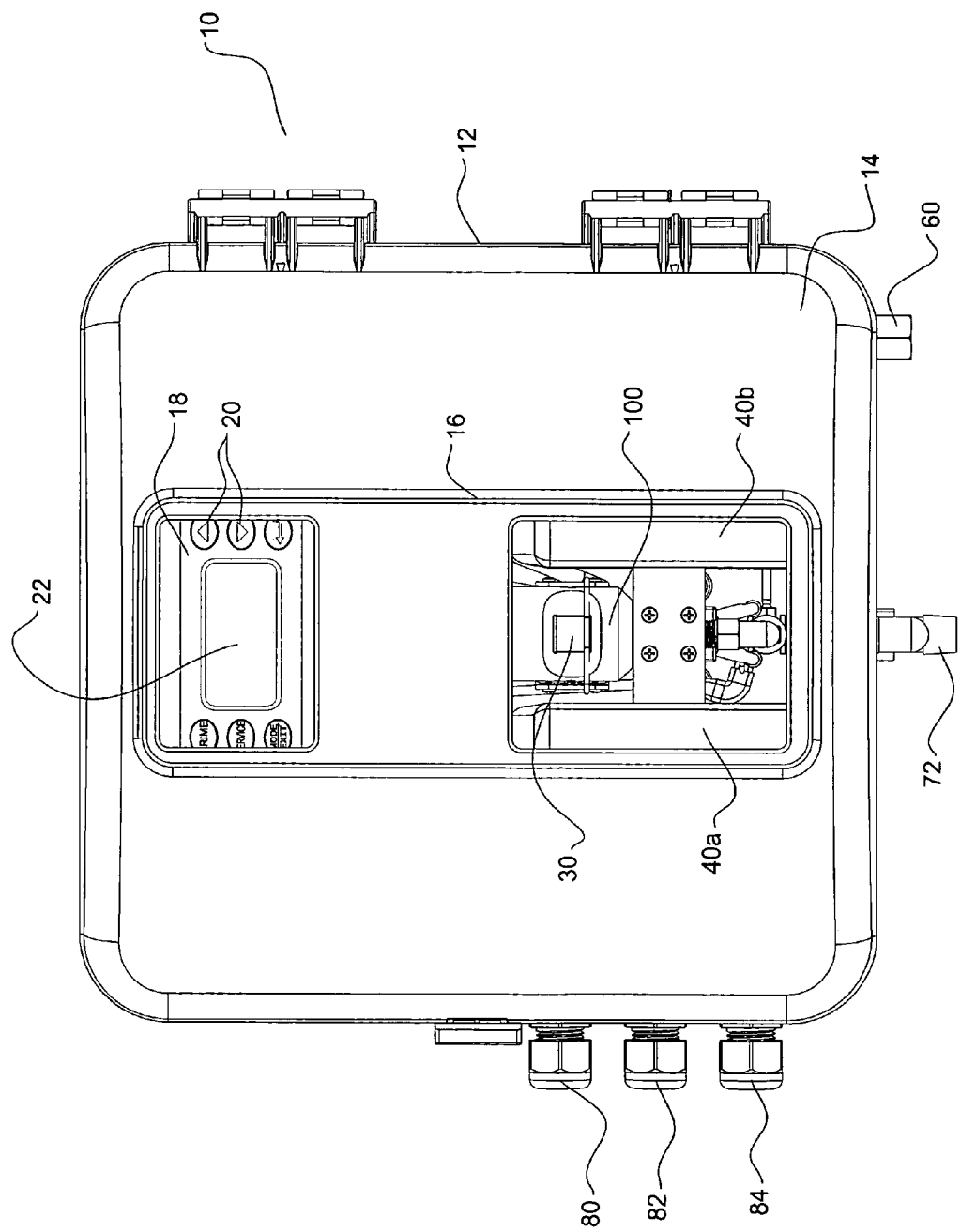
FIG. 1 is a front elevation view of an exemplary embodiment of a fluid content monitor constructed in accordance with the present disclosure, and which can be used, for example, to monitor the residual chlorine level in water.
Figure 2:
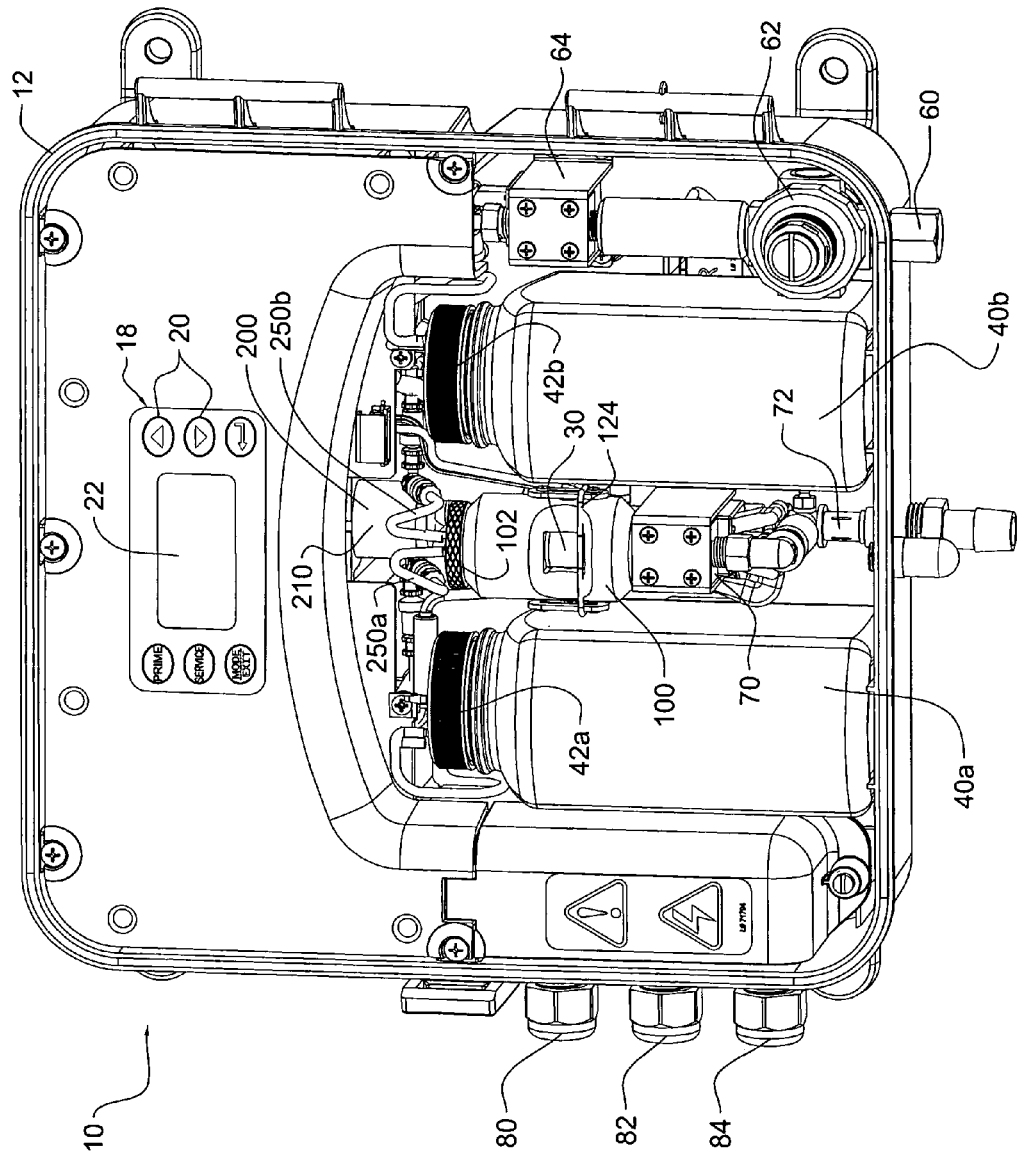
FIG. 2 is a front perspective view of the chlorine monitor of FIG. 1 shown with a cover removed to illustrate a pump assembly providing fluid connections between chemical reagent containers and a cuvette in a colorimeter.
Figure 3:
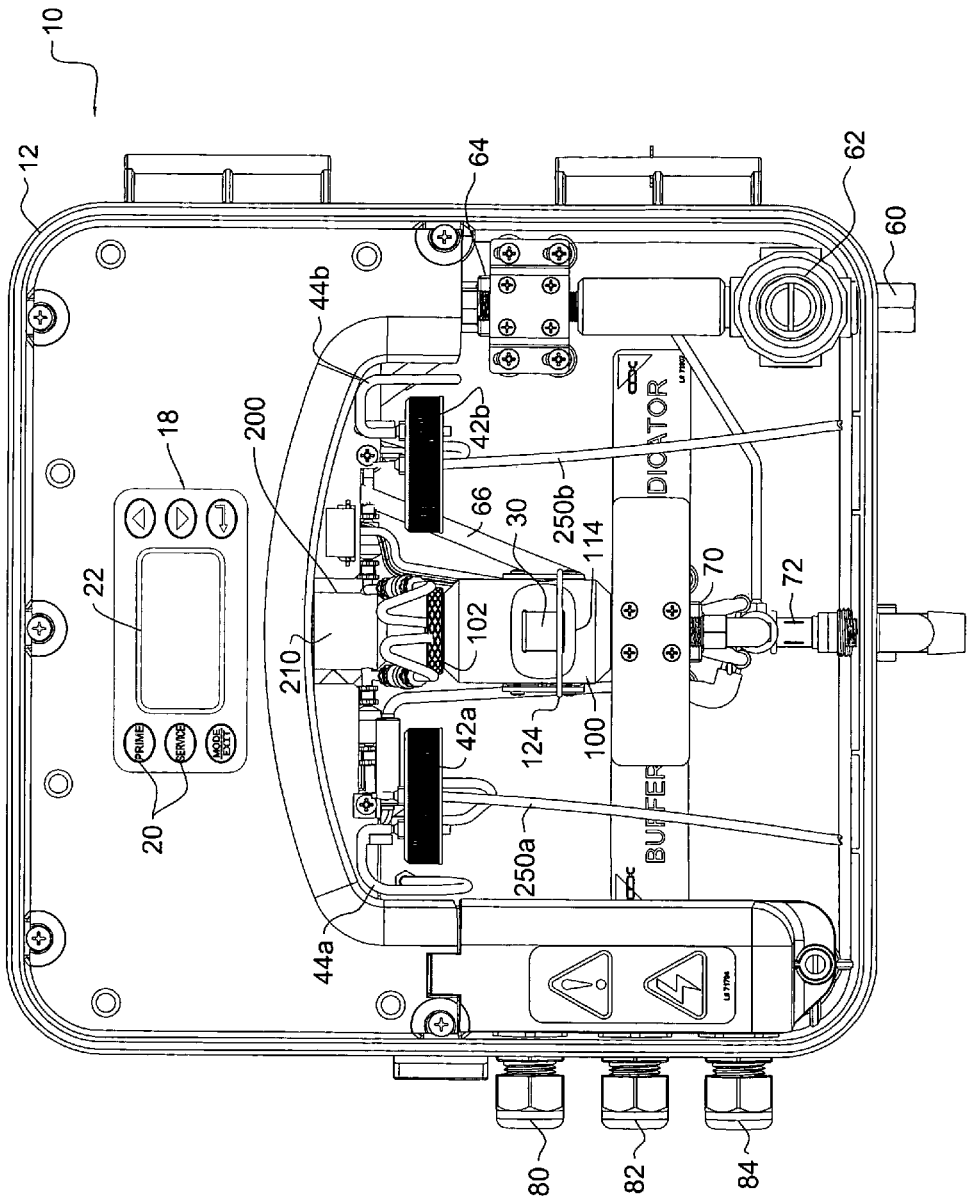
FIG. 3 is a front elevation view of the chlorine monitor of FIG. 1 shown with the cover and chemical reagent supplies removed.

Referring first to FIGS. 1-3, an exemplary embodiment of a fluid content monitor 10 constructed in accordance with the present disclosure is shown. The monitor 10 can be used, for example, to measure residual free or total chlorine levels in water. The monitor 10 is equally well-suited for other chemical or industrial processes but is described herein with respect to chlorine monitoring using calorimetric DPD (N,N-diethyl-p-phenylenediamine) chemistry.

The residual chlorine monitor 10 includes a strong, shatterproof case 12 with a removable front cover 14. The case 12 is also small in size relative to prior art monitors and corrosion-resistant to provide simple installation in a wide array of locations. As shown in FIG. 1, the front cover 14 defines a window 16 to allow operator monitoring and control. The window 16 provides access to a control panel 18 having touch pad controls 20 and a display panel 22. The viewing window 16 also allows inspection of a test sample holder or cuvette 30 that contains the fluid being tested.

Referring to FIG. 2, the residual chlorine monitor 10 is shown with the cover removed and removable first and second containers 40a, 40b for chemical reagents secured within the case 12, while in FIG. 3 the monitor 10 is shown with the containers removed. As shown in FIGS. 2 and 3, the monitor 10 includes a colorimeter 100 that receives the sample cuvette 30, and a pump assembly 200 for transferring the reagents from the reagent containers 402, 40b to the cuvette 30. As described in greater detail below, the cuvette 30 is removably mounted within the colorimeter 100 to allow for periodic cleaning or replacement. The calorimeter 100 measures the concentration of a known constituent, e.g., chlorine, of a solution by comparison with colors of standard solutions of that constituent.

Referring to FIGS. 2 and 3, the chlorine monitor 10 includes an inlet line 60 for receiving a water sample to be tested, and a pressure regulator 62 and inlet valve 64 for controlling flow of the water sample to the cuvette 30 for testing. A drain valve 70 controls flow from the cuvette 30 to a drain line 72 after testing has been completed. According to one exemplary embodiment, both the inlet valve 64 and the drain valve 70 are solenoid-actuated valves.

Electrical power is provided to the chlorine monitor 10 and to the various electrical and electronic components thereof through a connector 80 that extends through the case 12 as shown in FIGS. 1-3. In the exemplary embodiment shown, a second connector 82 allows the monitor 10 to be attached to one or more alarms (not shown), which are activated when the test results fall outside of predetermined parameters. A third connector 84 allows for on-line communication between the monitor 10 and a remote location.

Although not viewable in the drawings, the chlorine monitor 10 also includes an electronic controller (i.e., computer processor) that is operatively connected to the various components of the monitor 10. The controller is programmed to control: delivery of the water sample to the cuvette 30 using the water inlet valve 64; delivery of the reagents to the cuvette 30 using the pump assembly 200, testing of the sample using the calorimeter 100; and draining of the sample from the cuvette 30 after testing using a water drain valve 70. Signals representing photometric measurements provided by the calorimeter 100 are processed by the electronic controller, which then displays the results on the display panel 22. The control panel 18 allows the operator to program and run the residual chlorine monitor 10 according to parameters and operations programmed into the controller. Preferably, the electronic controller is a microprocessor located within the case 12 and is easily configured to exchange signals with other devices via a local area network and the like. In another embodiment, the electronic controller is remotely located from the chlorine monitor 10.

Figure 4:
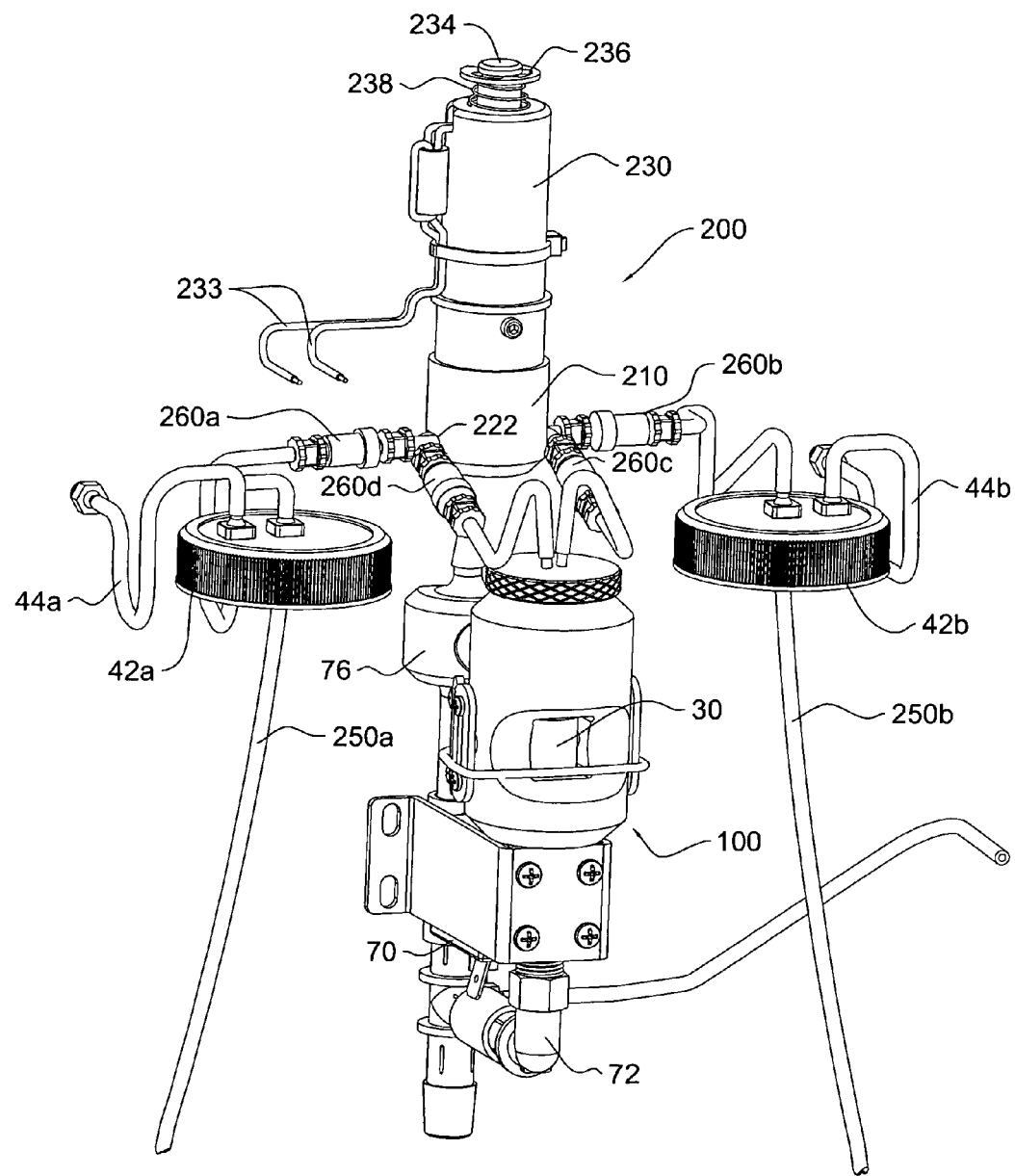
FIG. 4 is an front perspective view of the pump assembly and the colorimeter of the chlorine monitor of FIG. 1.
Figure 5:
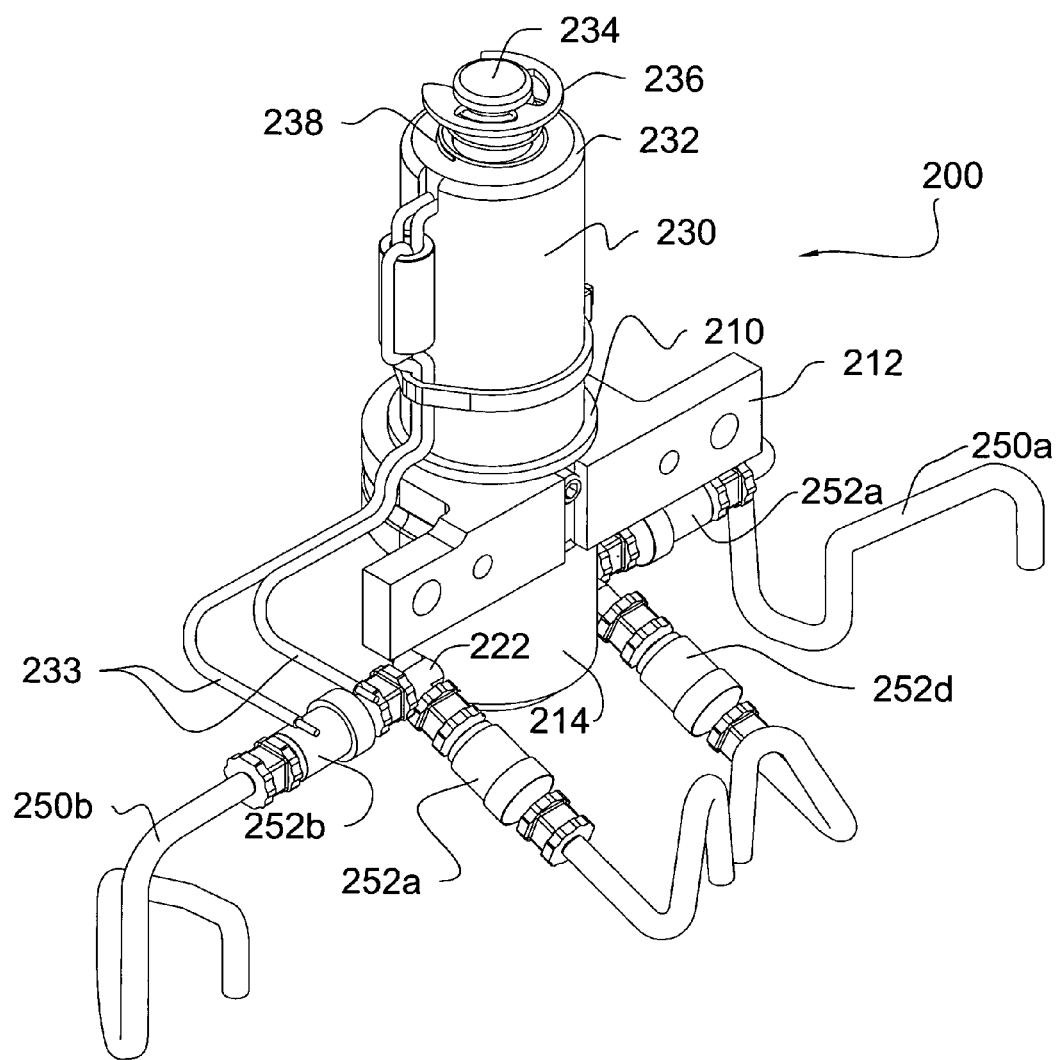
FIG. 5 is a rear perspective view of the pump assembly including a pump, a pump actuator, tubing, check valves, and a mounting bracket.
Figure 6:
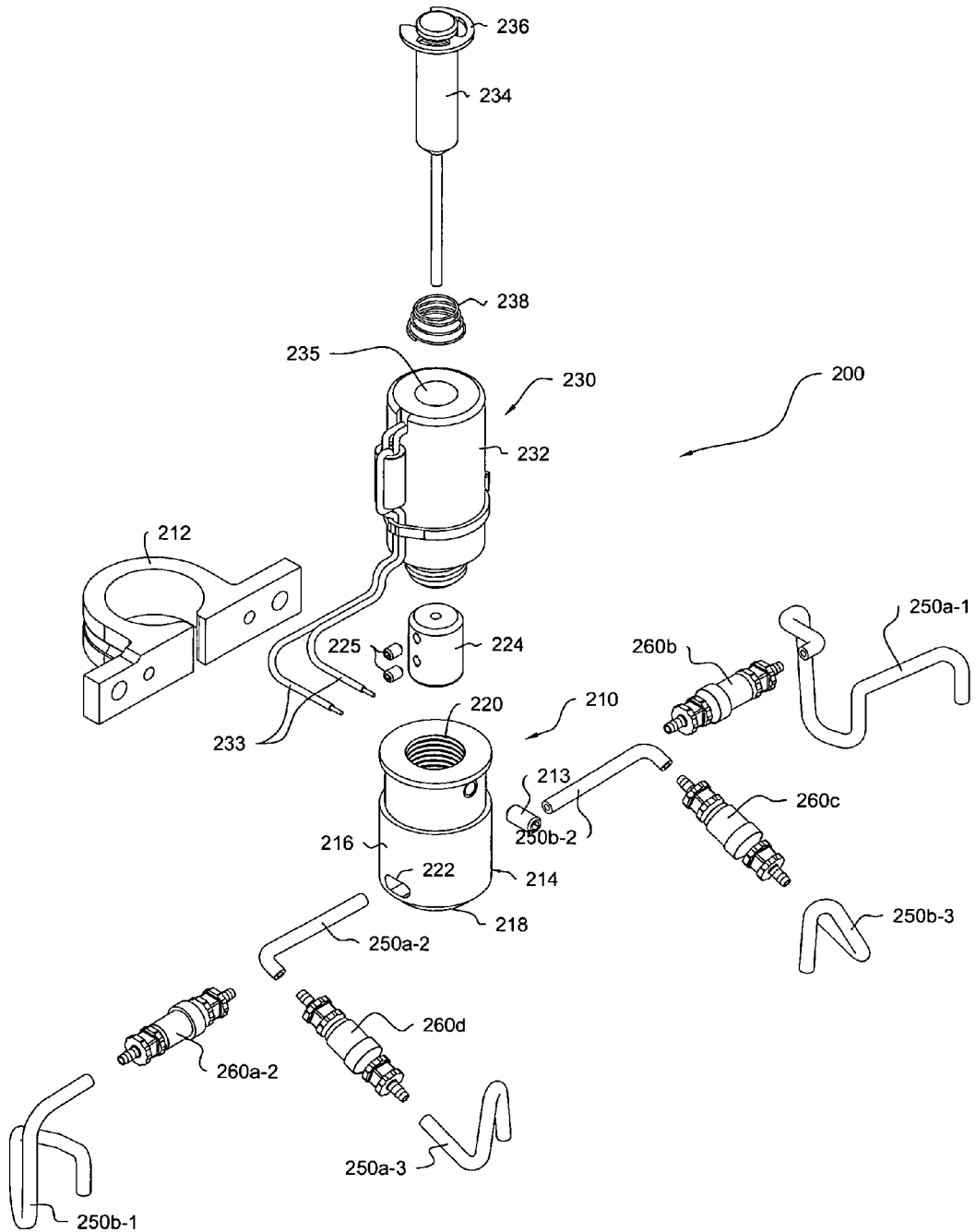
FIG. 6 is an exploded rear perspective view of the pump assembly minus the mounting bracket.

Referring to FIGS. 4-6, various detailed views of the pump assembly 200 are shown. The pump assembly 200 includes a pump 210, a pump actuator 230, first and second reagent tubes 250a, 250b, and check valves 260a-d. The pump assembly 200 delivers precisely measured and timed dosages of indicator reagent and buffer reagent to the water in the cuvette 30.

The pump 210 is mounted within the case 12 by a bracket 212 and includes a generally cup-shaped pump body 214 having a sidewall 216 extending from an end wall 218 to define an interior pump chamber 220. The sidewall 216 includes two openings 222 adjacent the end wall 218 for the reagent tubes 250a, 250b as described below. A housing 232 of the pump actuator 230 is secured to an entrance of the pump chamber 220 (with screw threads and a setscrew 213 for example), as best shown in FIG. 6. Referring to FIG. 6, the pump 210 also includes a pump hammer 224 within the chamber 220 of the body 214 for reciprocating linear movement between a retracted position moved away from the end wall 218 of the body, as shown in FIG. 7, and an extended position moved towards the end wall 218, as shown in FIG. 8.

Referring in particular to FIG. 6, the pump actuator 230 is a solenoid. The solenoid includes electromagnet coils (not viewable) located in the housing 232 that are electrically activated through pump solenoid wires 233 connected to the electronic controller. A magnetic armature 234 is slidably mounted within a central opening 235 of the housing 232, and the armature 234 is connected to the hammer 224 of the pump 210 (with set screws 225 for example) so that an electrical charge delivered to the solenoid 230 by the electronic controller causes linear movement of the armature 234. The upper end of the armature 234 carries a circumferential retaining ring 236, and a helical pump return spring 238 is disposed between the upper end of the housing 232 and the retaining ring 236. The return spring 238 normally biases the retaining ring 236 and the attached armature 234 into the retracted position shown in FIG. 7. The solenoid 230 is adapted to extend the hammer 224 of the pump 210 when energized and retract the hammer 224 when not energized.

With reference to FIGS. 3-6, the first reagent tube 250a connects the first reagent container 40a with the cuvette 30, and the second reagent tube 250b connects the second reagent container 40b with the cuvette 30. Both tubes 250a, 250b extend from the bottoms of the reagent containers 40a, 40b, through covers 42a, 42b of the reagent containers, pass through the openings 222 in the pump body 216, and continue to a nozzle 102. The nozzle 102 of the colorimeter 100 extends into the cuvette 30. Air vent tubes 44a, 44b also extend from the covers 42a, 42b. The openings 222 in the pump sidewall 216 are located so that the tubes 250a, 250b lay between the hammer 224 and the end wall 218 of the pump 210. Both tubes 250a, 250b include an inlet check valve 260a, 260b, respectively, between the reagent containers 40a, 40b and the pump 210, and an outlet check valve 260c, 260d, respectively, between the pump 210 and the colorimeter 100. The check valves 260a-d operate to limit the flow of reagent in a single direction from the reagent containers 40a, 40b to the cuvette 30 during the pumping cycle. The check valves 260a-d also prevent air from entering the tubes 250a, 250b during the pumping cycle.

To perform testing, the chlorine monitor 10 is primed, i.e., the reagents are added in equal proportion to a test sample in the cuvette 30. To prime the monitor 10, the pump 210 operates so that the reagents are delivered from their respective containers to the cuvette 30. Typically, the electronic controller is programmed to deliver signals to the pump actuator 230 so that the hammer 224 is repeatably driven between the retracted position shown in FIG. 7 and the extended position shown in FIG. 8.

In the extended position shown in FIG. 8, the hammer 224 squeezes the segments of the tubes 250a, 250b in the chamber 220 to a substantially closed position against the end wall 218 of the pump 210 to create pressure in the tubes 250a, 250b. Because the check valves 260a-d only allow flow towards the cuvette 30, the fluid in the tubes 250a, 250b is urged and moves toward the cuvette 30. When the hammer 224 returns to the retracted position shown in FIG. 7, the outlet check valves 260c, 260d prevent backflow and a vacuum is created in the tubes to draw the reagents in equal amounts from their respective containers 40a, 40b, through the inlet check valves 260a, 260b, and into the portions of the tubes 250a, 250b located between the inlet check valves 260a, 260b and the outlet check valves 260c, 260d.

Each tube 250a, 250b may comprise a single piece or may be formed by conically interconnected separate tube segments 1-3, as shown for example in FIG. 6 (the tube segments positioned in the reagent containers 40a, 40b are not shown in FIG. 6). Preferably, the tube segments 250a-2, 250b-2 located within the pump body 214 are resiliently flexible and are composed of silicone or similar material. The diameter may be selected to provide for a desired corresponding pumping pressure. The other tube segments 250a-1, 250a-3, 250b-1, 250b-3 may comprise a plastic such as polypropylene or other relatively rigid material. The diameter of the tubes 250a, 250b is normally relatively small so that excess reagent does not remain within the tube while the pump 210 is not in use. A smaller diameter also helps to facilitate pumping of the reagents through the respective check valves 260a-d.

In the exemplary embodiment shown, the tubes 250a, 250b have equal diameters and equal lengths such that equal amounts of buffer and indicator reagent are drawn through the pumping operation. The reagent containers 40a, 40b are thereby depleted together, which facilitates reagent replacement and maintenance of the chlorine monitor 10. In another embodiment, the separate tubes are combined by a T-shaped fitting to allow a single tube to pass through the pump 210 or a single tube to pass into the cuvette 30.

In another possible embodiment, the reagents are delivered in unequal amounts. One way to accomplish this is to provide duplicate metering pumps for each tube such that the electronic controller can direct compression of one or both tubes at a time. By independently compressing each tube the ratio of delivery can be modified as desired by the user. In other words, the reagents can be delivered in any ratio, which is determined by the ratio of respective hammer strikes. Further, using different size tubing for the tubes can more permanently vary the reagent ratio.

Figure 9:
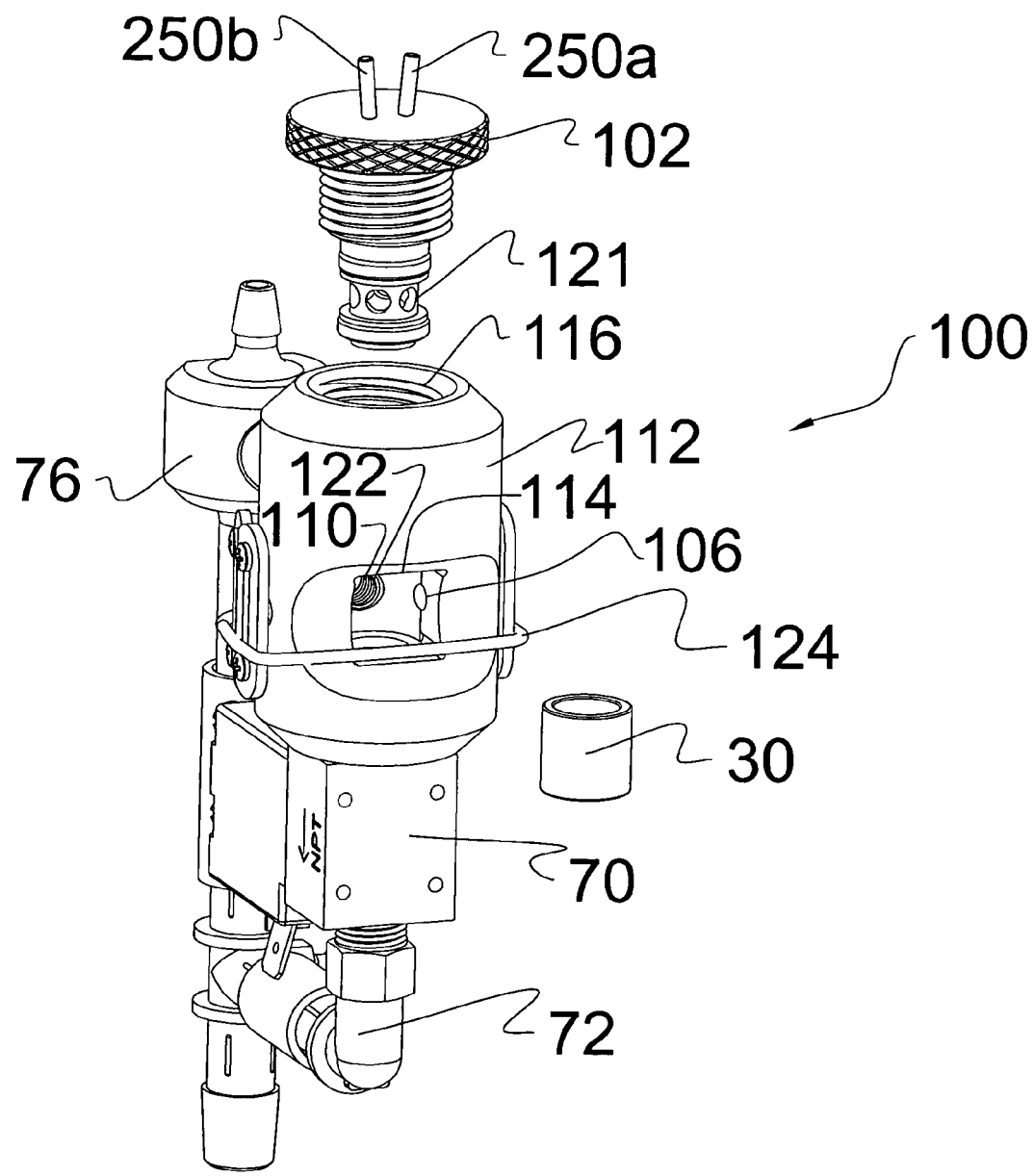
FIG. 9 is a front perspective view of the calorimeter, wherein the cuvette and a nozzle are shown removed from a body of the calorimeter.
Figure 10:
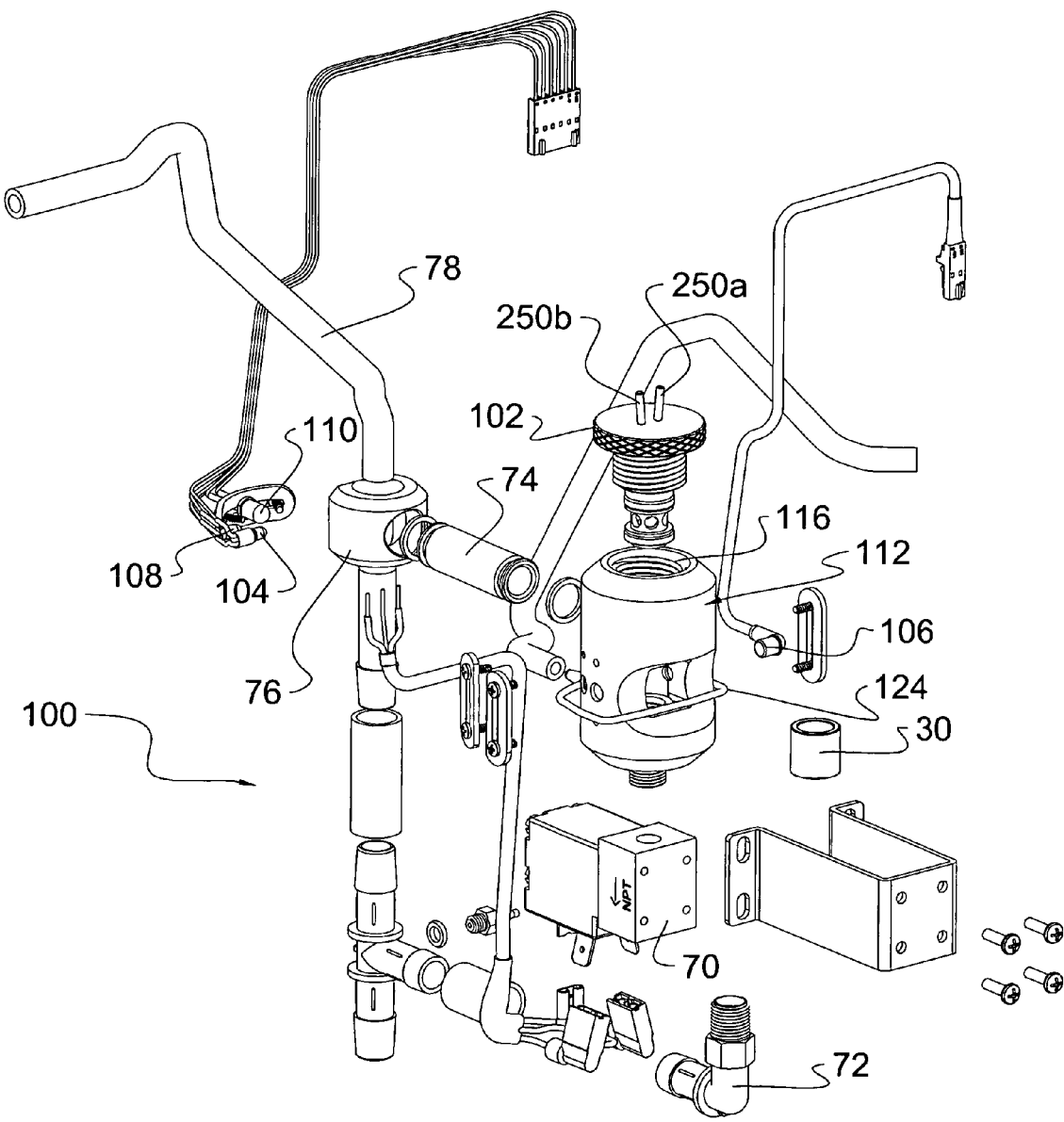
FIG. 10 is an exploded front perspective view of the colorimeter.
Figure 11:
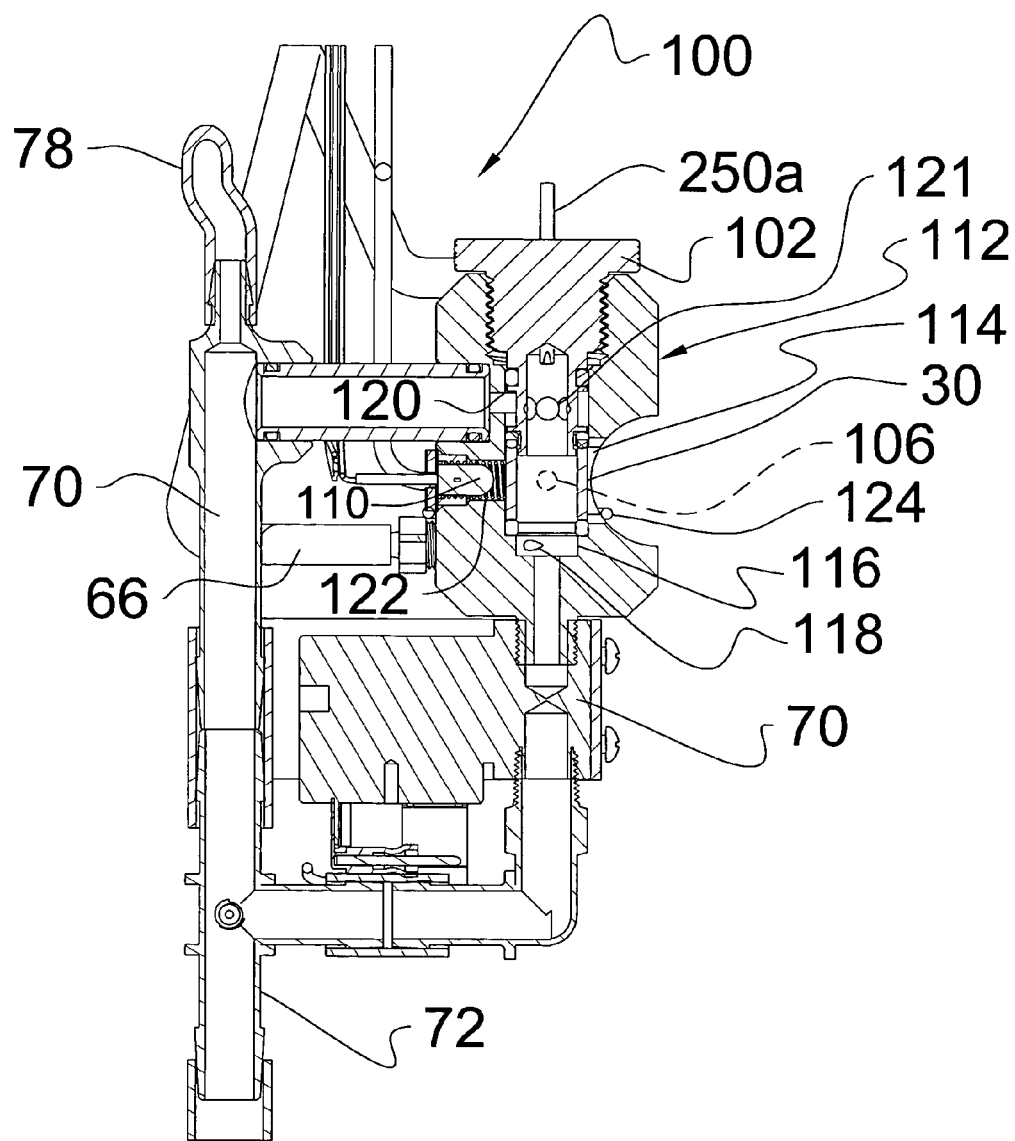
FIG. 11 is a sectional view of the colorimeter.

Referring now to FIGS. 9-11, the colorimeter 100 is shown in detail. Photometric components of the colorimeter 100, which are shown best in FIG. 10, include at least one light source 104 and a light detector or photodiode 106, for performing colorimetric testing of the sample within the cuvette 30. The primary light source 104 for measuring the level or concentration of chlorine may comprise, for example, a green light emitting diode (LED) 104 providing a 515 nm light source. Typically, the photodiode 106 is positioned 180° from the primary light source 104. In operation, the primary light source 104 directs light through the sample water mixed with reagents in the cuvette 30 to the photodiode 106, which takes measurements representing the level or concentration of chlorine in the water and provides electronic signals representing these measurements. A secondary light source 108, which is also positioned 180° from the photodiode 106, is provided for sample level and flow measurement, and may comprise a red LED. The exemplary embodiment also provides a white LED 110 positioned behind the cuvette 30 to illuminate the cuvette 30 for viewing by an operator.

The calorimeter 100 includes a body 112 defining a cuvette portal 114 for removably receiving the cuvette 30, and a passageway 116 extending through the cuvette portal 114. The nozzle 102 is removably secured in the passageway 116 and is adapted to extend into the cuvette 30 when secured in the passageway 116 and lock the cuvette 30 in the passageway 116. In the exemplary embodiment shown, the nozzle 102 is secured with screw threads and can be loosened and tightened by hand to release and secure the cuvette 30 during cleaning or replacement of the cuvette 30. The cuvette 30 is substantially tubular and includes open ends 31a, 31b that align with the passageway 116 of the body 112.

The discharge ends of the tubes 250a, 250b enter the nozzle 102 at intersecting angles to provide improved mixing of the reagents. According to one exemplary embodiment a 10° angle is formed between the tubes 250a, 250b at the top of the nozzle 102. As shown best in FIG. 11, the body 112 of the calorimeter 100 further includes a sample port 118 intersecting the passageway 116. A tube 33 for the water sample is connected between the water inlet valve 64 (shown best in FIG. 3) and the sample port 118 of the colorimeter 100. The sample port 118 is offset from a central axis of the passageway 116 of the colorimeter 100 to promote a swirling effect and a mixing of the water and reagents. The sample port 118 extends into the passageway 116 below the cuvette 30.

As shown best in FIG. 11, the body 112 of the colorimeter 100 also has an overflow port 120 intersecting the passageway 116 above the cuvette 30. The nozzle 102 includes side openings 121 for overflow from the cuvette 30 to flow through the overflow port 120 to overflow tubes 74, 76 connected to the drain 71 (an air vent tube 78 is connected to the overflow tubes and drain).

As shown best in FIGS. 9 and 11, the calorimeter 100 includes a spring 122 for ejecting the cuvette 30 out of the cuvette portal 114 upon removal of the nozzle 102 from the cuvette 30. A resiliently flexible retainer 124 is provided in front of the portal 114 for supporting the ejected cuvette 30 so that the cuvette 30 is not allowed to fall and be damaged.

The illustrated embodiments can be understood as providing exemplary features of certain embodiments, and therefore, components and/or aspects of the illustrations can be, without limitation, otherwise combined, interconnected, sequenced, separated, interchanged, positioned, and/or rearranged without materially departing from the disclosed systems or methods. For example, the nozzle and/or discharge tubes may or may not extend into the cuvette. In other embodiments, the discharge tubes may combine the reagent (s) with the fluid remotely from the cuvette and/or the nozzle would facilitate the mixing at another point. For another example, it is envisioned that the reagent(s) can be selected to interact with, and thus monitor, a plurality of compounds independently and collectively such as lead, fluoride and the like.

From the foregoing it may be seen that the present disclosure provides for a fluid content monitor 10 with a solenoid-operated pump assembly 200 and a colorimeter 100 including a removable cuvette 30. While this disclosure has provided a detailed description of exemplary embodiments, numerous modifications and variations of the fluid content monitor 10, pump assembly 200, and calorimeter 100, all within the scope of the disclosure, will readily occur to those skilled in the art. Accordingly, it is understood that this description is illustrative only of the principles of the disclosure and is not limitative thereof.

What is claimed is:

1. A fluid content monitor comprising:
 a light transparent cuvette adapted to receive a fluid sample;
 a colorimeter adapted to direct light through the cuvette, receive the light passing through the cuvette, and generate a signal indicative of contents of the fluid sample based upon the received light;
 a container for holding a reagent; and
 a pump assembly including:
 a body having a side wall extending from an end wall to define a chamber, and openings in the side wall adjacent the end wall,
 a hammer mounted within the chamber of the body for reciprocating linear movement between a retracted position moved away from the end wall and an extended position moved against the end wall,
 an actuator operatively connected to the hammer,
 a reagent tube extending from the container to the cuvette for delivering reagent to the cuvette, wherein a resiliently flexible section of the reagent tube passes through the openings in the side wall of the pump body and extends through the chamber between the hammer and the end wall such that the resiliently flexible section is open when the hammer is in the retracted position and substantially closed when the hammer is in the extended position,
 an inlet check valve carried by the reagent tube between the reagent container and the pump to prevent reverse flow to the reagent container, and
 an outlet check valve carried by the reagent tube between the pump and the cuvette to prevent reverse flow to the pump.

2. A monitor as recited in claim 1, wherein the actuator comprises a solenoid having an armature connected to the hammer.

3. A monitor as recited in claim 2, wherein the solenoid is adapted to extend the hammer of the pump when energized and retract the hammer when not energized.

4. A monitor as recited in claim 1, further comprising a second container for holding a second reagent, and a second reagent tube extending from the container to the cuvette through the openings in the side wall of the pump body for delivering the second reagent to the cuvette such that the second reagent tube is open when the hammer is in the retracted position and substantially closed when the hammer is in the extended position, wherein the second reagent tube also includes an inlet check valve and an outlet check valve.

5. A monitor as recited in claim 4, wherein ends of the tubes extend into the cuvette at intersecting angles.

6. A monitor as recited in claim 1, wherein the reagent tube comprises multiple segments successively connected together.

7. A monitor as recited in claim 1, wherein the calorimeter includes a body defining a cuvette portal for removably receiving the cuvette.

8. A monitor as recited in claim 7, wherein the body of the colorimeter includes a passageway extending through the cuvette portal, and the colorimeter further includes a nozzle receiving an end of the reagent tube and removably secured in the passageway, wherein the nozzle is adapted to selectively lock the cuvette in the calorimeter and mix the reagent and the fluid sample.

9. A monitor as recited in claim 8, wherein the body of the colorimeter further includes a sample port intersecting the passageway, wherein the sample port is offset from a central axis of the passageway.

10. A monitor as recited in claim 8, wherein the colorimeter includes a spring adapted to eject the cuvette out of the cuvette portal upon removal of the nozzle from the cuvette.

11. A monitor as recited in claim 10, wherein the cuvette is substantially tubular and defines open ends which align with the passageway of the body.

12. A monitor as recited in claim 1, wherein the calorimeter includes a red light emitting diode (LED) for chlorine measurement, a green LED for flow measurement, and a white LED for visual inspection.

13. A fluid content monitor comprising:
 a light transparent cuvette adapted to receive a fluid sample;

a nozzle connected to the cuvette for introducing reagent into the cuvette;

a colorimeter adapted to direct light through the cuvette, receive the light passing through the cuvette, and generate a signal indicative of contents of the fluid sample based upon the received light;

a first container for holding a first reagent;

a second container for holding a second reagent; and a pump assembly including:

a body having a side wall extending from an end wall to define a chamber, and openings in the side wall adjacent the end wall, a hammer mounted within the chamber of the body for reciprocating linear movement between a retracted position moved away from the end wall and an extended position moved against the end wall, an actuator operatively connected to the hammer, a first reagent tube in fluid communication with the first container and the nozzle for delivering the first reagent to the cuvette, wherein a resiliently flexible section of the first reagent tube passes through the openings in the side wall of the pump body such that the respective resiliently flexible section is open when the hammer is in the retracted position and substantially closed when the hammer is in the extended position, a second reagent tube in fluid communication with the second container and the nozzle for delivering the second reagent to the cuvette, wherein a resiliently flexible section of the second reagent tube passes through the openings in the side wall of the pump body such that the respective resiliently flexible section is open when the hammer is in the retracted position and substantially closed when the hammer is in the extended position, and an inlet check valve carried by the each reagent tube between the respective reagent container and the pump to prevent reverse flow to the reagent containers.

* * * * *